(12) United States Patent
Gorochow (10) Patent No.: US 11,051,825 B2
(45) Date of Patent: Jul. 6, 2021

(54) DELIVERY SYSTEM FOR EMBOLIC BRAID (71) Applicant: DePuy Synthes Products, Inc., Raynham, MA (US)

(72) Inventor: Lacey Gorochow, Raynham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 153 days.

(21) Appl. No.: 16/058,918

(22) Filed: Aug. 8, 2018

(65) Prior Publication Data

US 2020/0046370 A1    Feb. 13, 2020

(51) Int. Cl.
| | |
|---|---|
| A61B 17/12 | (2006.01) |
| A61B 90/00 | (2016.01) |
| A61B 17/00 | (2006.01) |
| A61M 25/00 | (2006.01) |
| A61F 2/82 | (2013.01) |

(52) U.S. Cl.
CPC .. *A61B 17/12168* (2013.01); *A61B 17/12113* (2013.01); *A61B 2017/00862* (2013.01); *A61B 2017/00951* (2013.01); *A61B 2017/12054* (2013.01); *A61B 2090/3966* (2016.02); *A61M 2025/0037* (2013.01)

(58) Field of Classification Search
CPC ........ A61B 17/12168; A61B 17/12172; A61B 17/12113; A61B 2017/12054; A61F 2/95; A61F 2/011; A61F 2002/9505; A61F 2002/9511
See application file for complete search history.

(56) References Cited

U.S. PATENT DOCUMENTS

| | | |
|---|---|---|
| 6,391,037 B1 | 5/2002 | Greenhalgh |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |

(Continued)

FOREIGN PATENT DOCUMENTS

| | | |
|---|---|---|
| EP | 3 517 055 A1 | 7/2019 |
| WO | 2013/162817 A1 | 10/2013 |
| WO | 2014/078286 A1 | 5/2014 |

OTHER PUBLICATIONS

Partial European Search Report issued in corresponding European Patent Application No. 19 19 0490 dated Dec. 20, 2019.

*Primary Examiner* — Majid Jamialahmadi
(74) *Attorney, Agent, or Firm* — Troutman Pepper Hamilton Sanders LLP (57) ABSTRACT

A device for treating an aneurysm by releasing an implanted implant from a delivery system at a treatment site can include a braided implant attached to a releasing component that can be detachably engaged with a delivery tube and a pull wire. The releasing component can engage the delivery tube in a compressed configuration via friction fit and can disengage the delivery tube by expanding to a released or deployed configuration. The pull wire can have an extending portion that can engage the releasing component and an elongated portion that can be pulled to disengage the releasing component. The braided implant, once implanted, can be released from the delivery tube by disengaging the pull wire from the releasing component and disengaging the releasing component from the delivery tube.

14 Claims, 10 Drawing Sheets

(56) References Cited

U.S. PATENT DOCUMENTS

| | | |
|---|---|---|
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 10,517,604 B2 | 12/2019 | Bowman et al. |
| 2006/0064151 A1 | 3/2006 | Guterman |
| 2008/0281350 A1 | 11/2008 | Sepetka |
| 2010/0211156 A1* | 8/2010 | Linder ............... A61F 2/95 623/1.11 |
| 2010/0324649 A1 | 12/2010 | Mattsson |
| 2012/0283768 A1 | 11/2012 | Cox et al. |
| 2014/0135812 A1 | 5/2014 | Divino et al. |
| 2014/0200607 A1 | 7/2014 | Sepetka et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |

\* cited by examiner

DELIVERY SYSTEM FOR EMBOLIC BRAID

FIELD OF INVENTION

This disclosure relates to medical instruments, and more particularly, delivery systems for a device for aneurysm therapy.

BACKGROUND

Aneurysms can be complicated and difficult to treat. For example, treatment access can be limited or unavailable when an aneurysm is located proximate critical tissues. Such factors are of concern with cranial aneurysms due to the presence of brain tissue surrounding cranial vessels.

Prior solutions have included endovascular treatment access whereby an internal volume of the aneurysm sac is removed or excluded from arterial blood pressure and flow. Alternative to endovascular or other surgical approaches can include occlusion devices that either fill the sac of the aneurysm with embolic material to create a thrombotic mass or to treat the entrance (or neck) of the aneurysm to minimize the blood flow across the entrance, induce venous stasis in the aneurysm, and facilitate a natural formation of a thrombotic mass within the aneurysm. Such devices typically utilize multiple embolic coils to either fill the sac or treat the entrance.

Obtaining a packing density sufficient to occlude an aneurysm by packing the aneurysm sac with embolic coils is difficult, time consuming, and aneurysm morphology (e.g. wide neck, bifurcation, etc.), and the like required ancillary devices such a stents or balloons to support the coil mass and obtain the desired packing density.

Naturally formed thrombotic masses formed by treating the entrance of the aneurysm with embolic coils can improve healing compared to aneurysm masses packed with embolic coils by reducing possible distention from arterial walls and permitting reintegration into the original parent vessel shape along the neck plane. However, embolic coils delivered to the neck of the aneurysm can potentially have the adverse effect of impeding the flow of blood in the adjoining blood vessel; at the same time, if the entrance is insufficiently packed, blood flow can persist into the aneurysm.

Furthermore, embolic coils do not always effectively treat aneurysms as aneurysms treated with multiple coils often recanalize or compact because of poor coiling, lack of coverage across the aneurysm neck, blood flow, or even aneurysm size.

Several examples of an occlusion device are described in U.S. Pat. No. 8,998,947. However, this approach relies upon the use of embolic coils or mimics the coil approach to obtain a safe packing density and therefore unnecessarily risks rupture of the aneurysm. Furthermore, this approach fails to teach a delivery system whereby an occlusion device can be re-positioned after initial positioning of its aneurysm occlusion structure to ensure patient safety associated with precise positioning.

It is therefore desirable to have a device which easily, accurately, and safely occludes a neck of an aneurysm or other arterio-venous malformation in a parent vessel without blocking flow into perforator vessels communicating with the parent vessel.

Further, once deployed into the aneurysm, the surgeon requires positive confirmation that the device has been positively released. Certain prior art release mechanisms have difficulties detaching, leading to misplacement of the device.

SUMMARY

Disclosed herein are various exemplary devices and systems of the present invention that can address the above needs. The devices generally can include a braided implant attached to a releasing component that can be detachably engaged with a delivery tube and a pull wire. The releasing component can engage the delivery tube in a compressed configuration and can disengage the delivery tube by expanding to a released or deployed configuration. The pull wire can have an extending portion that can engage the releasing component and an elongated portion that can be pulled to disengage the releasing component. The braided implant, once implanted, can be released from the delivery tube by disengaging the pull wire from the releasing component and disengaging the releasing component from the delivery tube.

In one example, a system can include a braided implant, a delivery tube, a releasing component, and a pull wire. The delivery tube can have a lumen therethrough, a distal end, an outer surface, and a channel on the outer surface. The releasing component can have a band and a spring member attached to the band. The band can be attached to a first portion of the braided implant, and the spring member can be movable from a compressed configuration that presses the outer surface of the delivery tube and an extended configuration that extends away from the outer surface of the delivery tube. The pull wire can be positioned within the channel of the delivery tube and can be movable from an engaging configuration to a releasing configuration. The engaging configuration can engage the releasing component, and the releasing configuration can allow the spring member to expand to its extended configuration.

The braided implant can have a first portion and a second portion separated by a fold. The first portion can encompass a portion of the outer surface of the distal end of the delivery tube. The second portion can have an elongated tubular structure and can be positioned within the lumen of the delivery tube.

The pull wire can have an extending portion and an elongated portion, and a movement of the elongated portion can move the extending portion from the engaging configuration to the releasing configuration. The pull wire can be fastened to the channel of the delivery tube with an adhesive, and the movement of the elongated portion can break the adhesive to unfasten the pull wire.

The system can include an affixing component that affixes the braided implant to the outer surface of the band of the releasing component. The affixing component can include a lumen therethrough. The lumen can encompass the band of the releasing component.

The spring member can be an elongated member having a proximal end and a distal end. The proximal end can attach to a distal surface of the band of the releasing component. The distal end can press the outer surface of the delivery tube in the compression configuration, and the distal end can extend away from the outer surface of the delivery tube in the extended configuration.

The releasing component can have an occlusion member attached to the band that can be movable from a delivery configuration to a deployed configuration. The delivery configuration can extend longitudinally along the outer surface of the delivery tube, and the deployed configuration can at least partially obstruct the lumen of the band.

The releasing component can be composed of a radiopaque material.

An example device for treating an aneurysm can have a tubular delivery member, a braided tubular implant, a releasing component, and a bending member. The tubular delivery member can have a distal delivery end, an interior, and an exterior. The braided tubular implant can have a distal implant end that can extend outward from the distal delivery end of the tubular delivery member and fold proximally over a portion of the exterior of the tubular delivery member. The braided tubular implant can have a proximal implant end that can be positioned within the interior of the tubular delivery member. The releasing component can be attached to the distal implant end of the braided implant and detachably attached to the exterior of the tubular delivery member near the distal delivery end. The bending member can be positioned near the distal delivery end of the tubular delivery member. The bending member can have a bent configuration and a straight configuration. The bent configuration can engage a distal surface of the releasing component, and the straight configuration can disengage the distal surface of the releasing component.

The releasing component can have an attached configuration and a deployed configuration. The attached configuration can engage the exterior of the tubular delivery member, and the deployed configuration can disengage the exterior of the tubular delivery member.

The deployed configuration can at least partially occlude the lumen of the band of the releasing component.

The bending member can be the extending portion of a pull wire, and a movement of an elongated portion of the pull wire can move the extending portion from the bent configuration to the straight configuration. The pull wire can be positioned within a channel on the exterior of the tubular delivery member. The pull wire can be fastened to the tubular delivery member with an adhesive, and the movement of the elongated portion can break the adhesive to unfasten the pull wire.

An example method for releasing an implant at an aneurysm treatment site can include the steps of providing a braided implantation delivery system, engaging a pull wire of the delivery system to a releasing component of the delivery system, engaging the releasing component to a delivery tube of the delivery system, implanting a braided implant of the delivery system at the treatment site, pulling the pull wire to disengage from the releasing component, disengaging the releasing component from the delivery tube, and releasing the releasing component from the delivery tube thereby releasing the braided implant from the delivery tube.

The step of releasing the releasing component can include the step of moving a spring member of the releasing component from an engaged configuration engaging an outer surface of the delivery tube to a released configuration extending away from the outer surface of the delivery tube.

The step of implanting the braided implant can include forming an occlusive sack by inverting a portion of the braided implant.

The method can include the step of fastening the pull wire to the delivery tube with an adhesive. The step of pulling the pull wire can include the step of breaking the adhesive.

The method can include the step of moving a movable member of the releasing component to at least partially occlude a lumen of the releasing component.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Previous approaches utilizing embolic coils can be improved upon by treating the aneurysm entrance and/or packing the aneurysm with an embolic braided implant. For example, see U.S. patent application Ser. No. 15/903,860, incorporated herein by reference. Treating the aneurysm with the braided implant can have potential advantages over treatments utilizing embolic coils such as a higher packing density, ability to retract and reposition the implant during the implantation procedure, ability to perform implantation without ancillary devices such as stents or balloons, reduced risk of reanalyzing or compacting, and improved coverage across the aneurysm neck, for example.

In braided implant delivery systems, it can be advantageous to maintain an attachment between the implant and the delivery system until the implant is in place at the treatment site, then detach the implant so that the delivery system can be extracted. The present disclose describes various example systems, devices, and methods that can be utilized for at least this purpose.

Figure 1A:
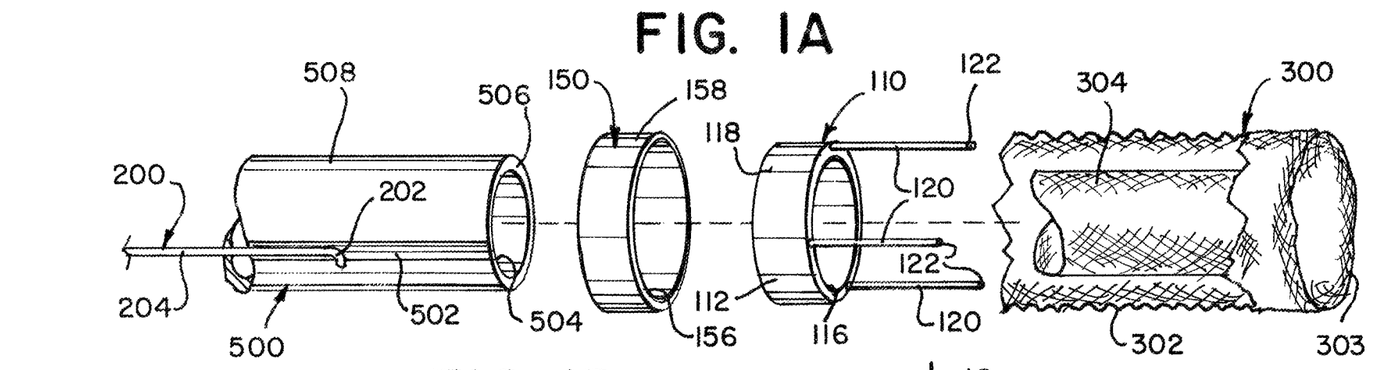
FIG. 1a is an exploded view depicting components of an exemplary device of the present invention.
Figure 1B:
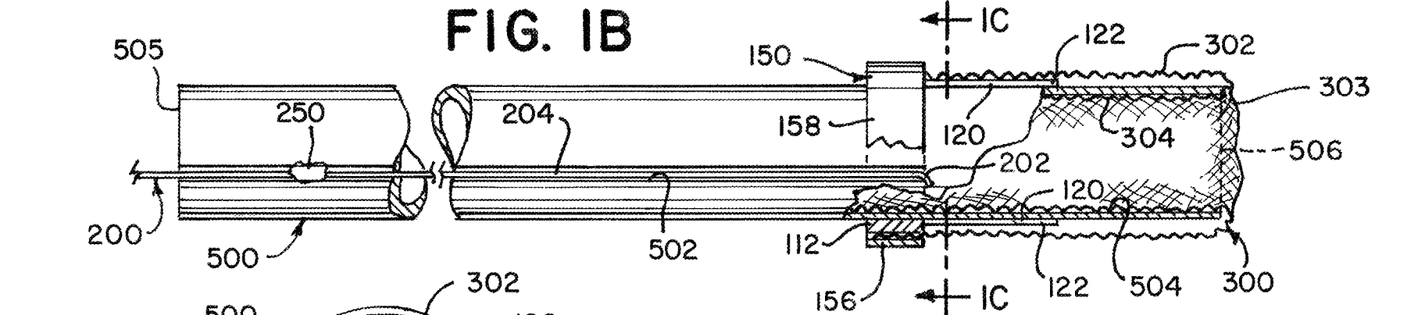
FIG. 1b is a cut-away view of an exemplary device of the present invention.
Figure 1C:
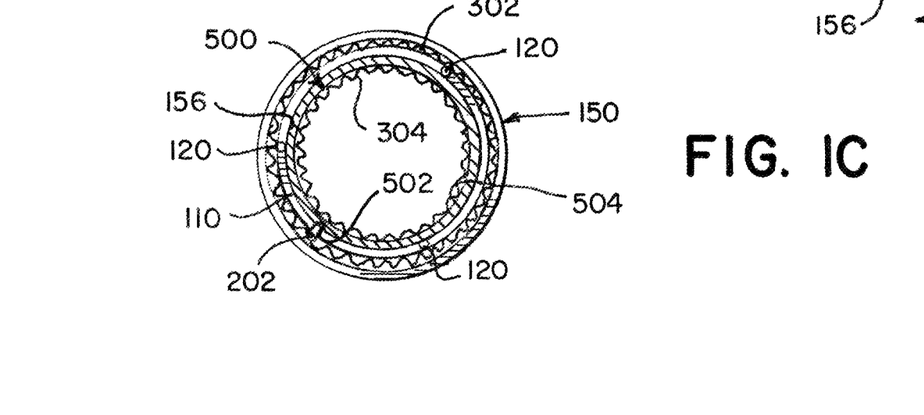
FIG. 1c is a cross-sectional view of an exemplary device of the present invention

FIGS. 1a to 1c illustrate an exemplary delivery system configured for delivery through a microcatheter to a treatment site. FIG. 1a is an exploded view depicting components of the exemplary delivery system. FIG. 1b is a cut-away view depicting the assembled exemplary delivery system including components shown in FIG. 1a. FIG. 1c is a cross-sectional top-down view of the assembled system of FIG. 1b. As shown, the system can include a braided implant 300, a releasing component 110, an affixing component 150, a delivery tube 500, and a pull wire 200.

The braided implant 300 can have a substantially tubular structure having a fold 303 separating an outer fold 302 portion of the implant 300 from an inner fold 304 portion of the implant 300. The implant 300 can be folded such that the inner fold 304 is sized to fit within a lumen 504 of the delivery tube 500, the folded edge 303 rolls over a distal end 506 of the delivery tube 500, and the outer fold 302 fits over the delivery tube 500 extending proximally and attaching to the releasing component 110.

The releasing component 110 can be attached to the outer fold portion 302 of the braided implant 300 and can serve to attach the braided implant 300 to the delivery tube 500 during delivery to a treatment site and during implantation. After implantation is complete, the releasing component 110 can release the delivery tube so that it can be extracted from the patient.

FIGS. 1a to 1c show an example releasing component 110 in a compression configuration that can enable the releasing component 110 to attach the braided implant 300 to the delivery tube 500. Configured as shown in FIGS. 1a to 1c, the outer fold portion 302 of the braided implant 300 can fold over the releasing component 110 and attach to a band 112 of the releasing component 110. The band 112 can have a tubular structure including an outer surface 118 and a lumen 116, however other shapes are contemplated. The releasing component 110 can include one or more spring members 120 extending from the band and pressing against an outer surface 508 of the delivery tube 500, providing a friction fit between the releasing component 110 and the delivery tube 500. The spring members 120 can extend distally from a distal surface 114 the band and have distal ends 122 that press up against the delivery tube 500.

An affixing component 150 can be used to attach the releasing component 110 to the braided implant 300. The affixing component 150 can have an outer surface 158 and a lumen 156. The affixing component 150 can be placed over the band 112 of the releasing component 110, securing a portion of the outer fold 302 of the braided implant 300 between the affixing component 150 and the releasing component 110.

The delivery tube 500 can have a lumen 504 therethrough. The lumen 504 can contain the inner fold 304 of the braided implant 300. The lumen can also contain additional elements to facilitate the implantation of the braided implant 300 (not shown).

The delivery tube 500 can have a channel 502 travelling longitudinally on the outer surface 508, and the pull wire 200 can be positioned within the channel 502. The pull wire 200 can have an extending portion 202, such as a hook, that can engage the releasing component 110, and an elongated portion 204 that can be positioned within the channel 502, extending proximally. As shown, the extending portion 202 can extend across the distal surface 114 of the band 112. Engagement of the extending portion 202 with the releasing component can prevent distal movement of the releasing component 110 in relation to the delivery tube 500 and can thereby maintain the attachment between the braided implant 300 and the releasing component 110 until implantation of the braided implant 300 is completed.

The elongated portion 204 of the pull wire 200 can extend proximally beyond the proximal end 505 of the delivery tube 500, providing an operator of the system access to the pull wire 200. As shown in FIG. 1b, the pull wire 200 can be detachably attached to the delivery tube 500 with an adhesive 250. The adhesive 250 can inhibit movement of the pull wire 200 until sufficient force is applied to the pull wire 200 to break the adhesive 250.

FIG. 1c illustrates a cross-section view of the system near the distal end 506 of the delivery tube, proximal the fold 303 looking proximally as indicated in FIG. 1b. The inner fold 304 of the braided implant 300 can be positioned inside of the lumen 504 of the delivery tube 500; the releasing component 110 can be positioned over the outer surface 508 of the delivery tube 500; spring members 120 can extend from a distal surface 114 of the band 112 of the releasing component 110; the outer fold portion 302 can fit over the releasing component 110 attaching to the band 112 of the releasing component; and an affixing component 150 can fit over the band 112 of the releasing component and a portion of the outer fold 302 of the braided implant 300, affixing the braided implant 300 to the releasing component 110.

Figure 2A:
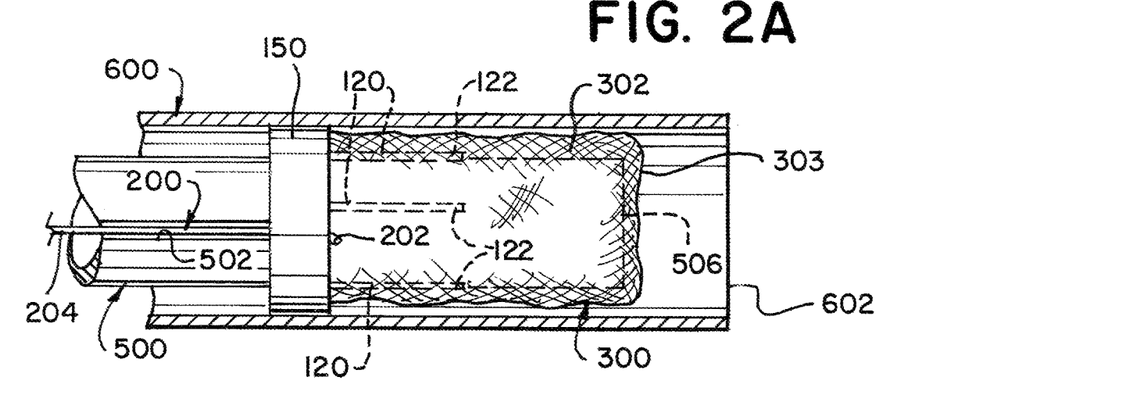
FIGS. 2a to 2g illustrate a method of use of a device of the present invention.

FIGS. 2a to 2g illustrate a method for deploying a braided implant 300 with a system or device according to the present invention. FIG. 2a illustrates a braided implant delivery system or device that can be provided. The system can include a braided implant 300, a delivery tube 500, a releasing component 110, and a pull wire 200. The system can be assembled as described in relation to FIGS. 1a to 1c such that the pull wire 200 is engaged with the releasing component 110 and the releasing component 110 is engaged to the delivery tube 500. The assembled system can be delivered to an aneurysm treatment site via a delivery catheter 600 such as a microcatheter.

Figure 2B:
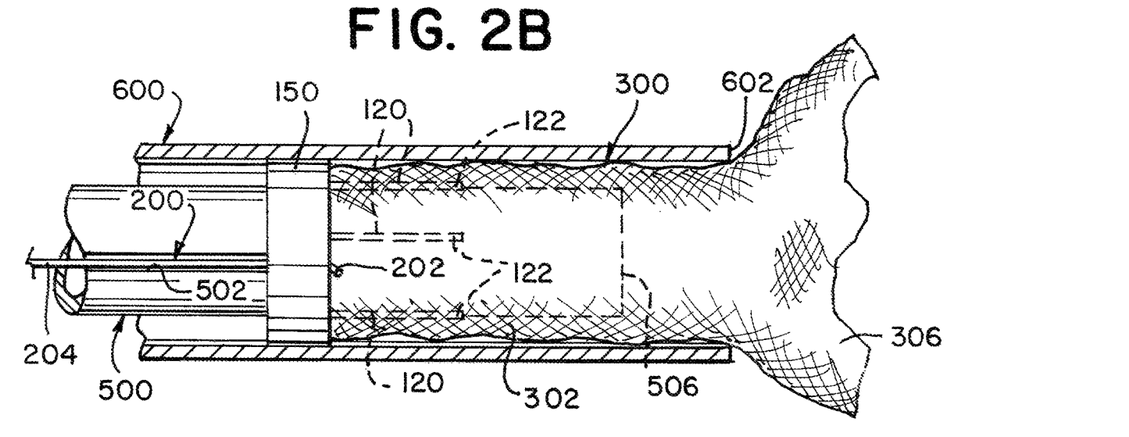

Once delivered, the braided implant 300 can be deployed, for example as described in U.S. patent application Ser. No. 15/903,860. FIG. 2b illustrates the braided implant 300 having an ejected portion 306 ejected from the distal end 602 of the delivery catheter 600. As shown, the braided implant 300 can remain attached to the delivery system such that at least a portion of the outer fold 302 remains inside the catheter 600. The braided implant 300 can remain attached to the delivery tube 500 so long as the releasing component 110 remains attached to the delivery tube 500. Before implantation of the braided implant is completed, the ejected portion 306 of the braided implant 300 can be retracted and repositioned.

Figure 2C:
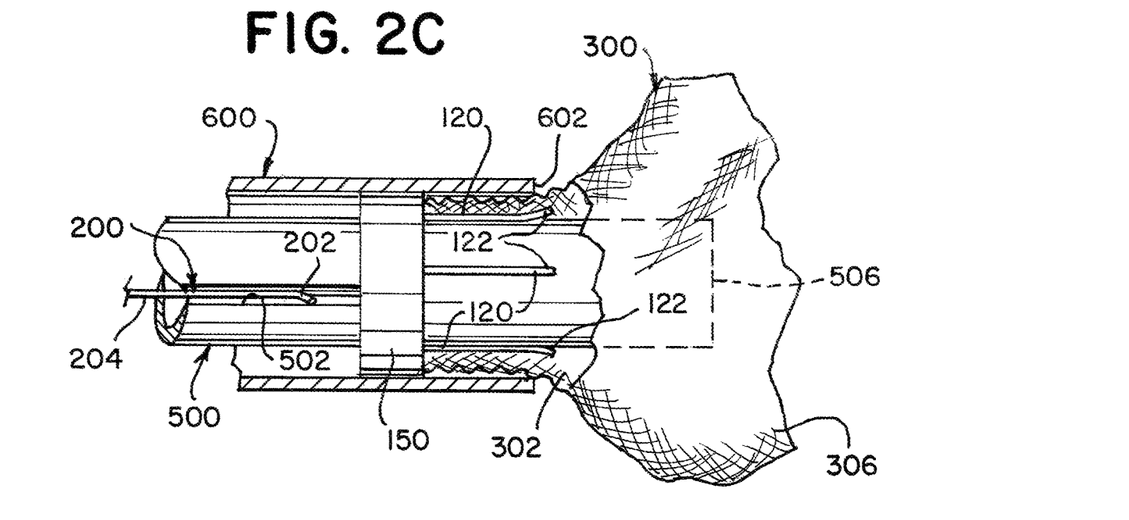

FIG. 2c illustrates steps that can be taken after implantation is complete to release the releasing component 110 from the delivery tube 500, thereby releasing the braided implant 300 from the delivery tube 500. FIG. 2c shows the pull wire 200 disengaged from releasing component 110 and the releasing component 110 beginning to move to a releasing configuration.

The extending portion 202 of the pull wire 200 can be flexible, and the extending portion 202 can disengage the releasing component 110 when the elongated portion 204 of the pull wire 200 is pulled proximally. Once disengaged, the pull wire 200 can be moved as to not inhibit distal movement of the releasing component 110 (in relation to the delivery tube).

The distal ends 122 of the spring members 120 can extend away from the delivery tube 500, moving from a compression configuration to an extended configuration. When in the spring members 120 are in the compression configuration, the spring members 120 can prevent movement of the releasing component 110 in relation to the delivery tube 500. The spring members 120 can be made of Nitinol or other memory shape material such that upon contacting a bodily fluid, such as blood, the spring members 120 can move to a predetermined shape that extends away from the delivery tube 500. FIG. 2c shows the delivery tube 500 moved distally in relation to the catheter, so that the delivery system begins to exit the catheter 600, thereby exposing the distal ends 122 of the spring members 120.

Figure 2D:
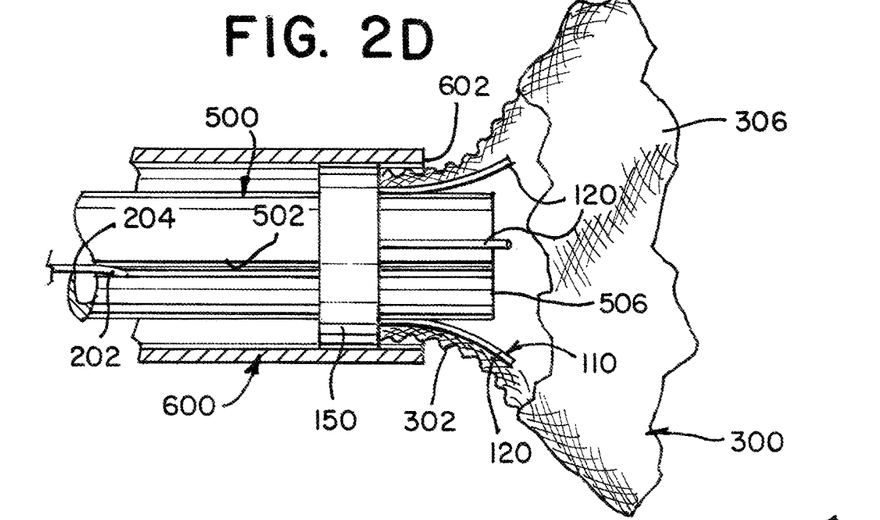

FIG. 2d illustrates the spring members 120 continuing to move into a releasing configuration as they exit the catheter 600. The spring members 120 can press against the braided implant 300, extending portions of the implant 300, for example to occlude a treatment site opening such as the neck of an aneurysm.

Figures 2E, 2F:
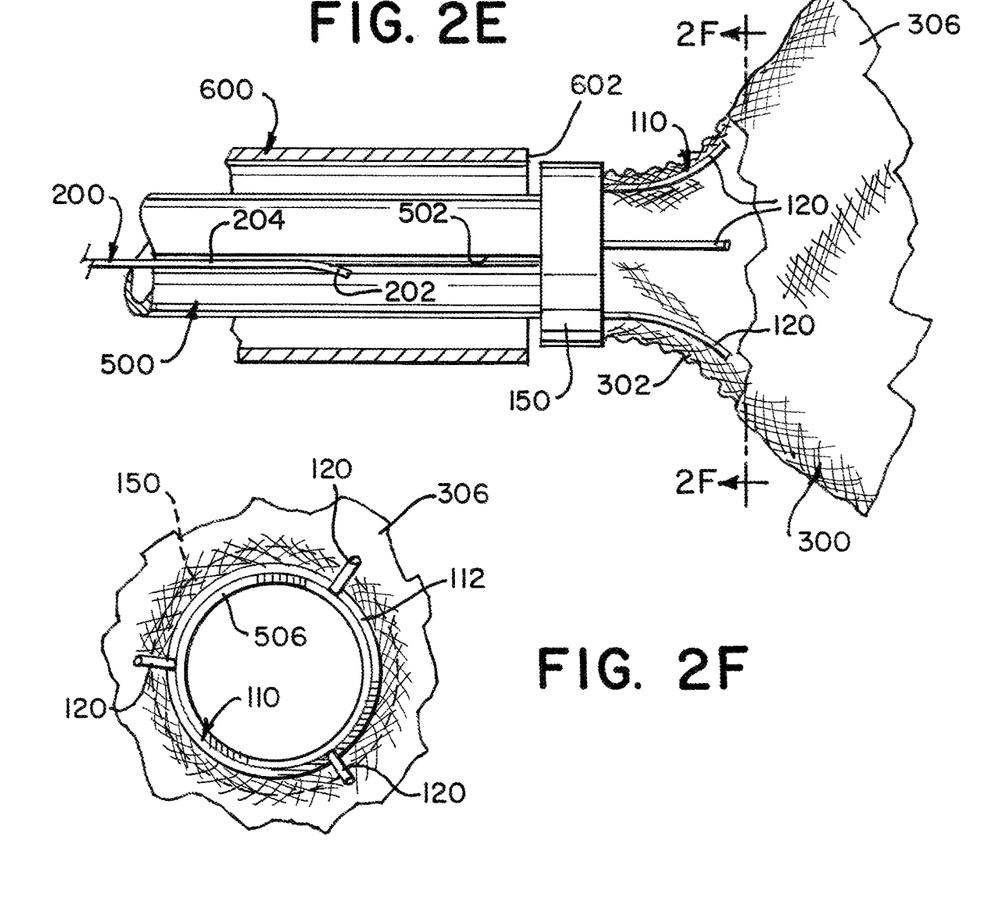

FIG. 2e illustrates the releasing component 110 sliding off the distal end 506 of the delivery tube 500. FIG. 2f is a cross-sectional view looking proximally as indicated in FIG. 2e. The band 112 of the releasing component 110 is shown encompassing the distal end 506 of the delivery tube 500 as the spring members 120 extend outward.

Figure 2G:
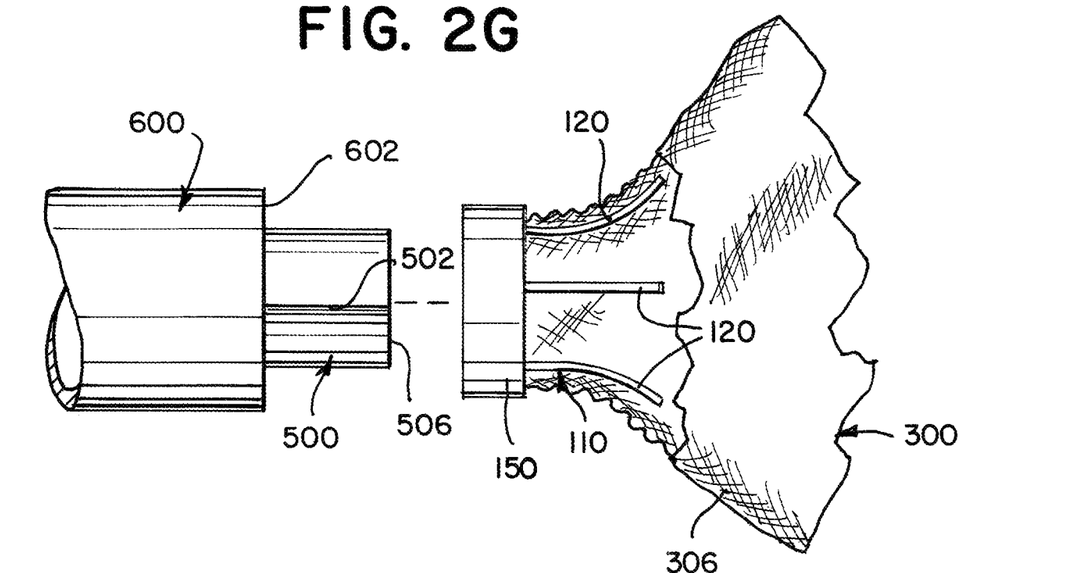

FIG. 2g illustrates the releasing component 110 separated from the delivery tube 500. Once disengaged, the delivery tube 500 can be extracted while the braided implant 300 and releasing component 110 remain implanted.

Figure 3A:
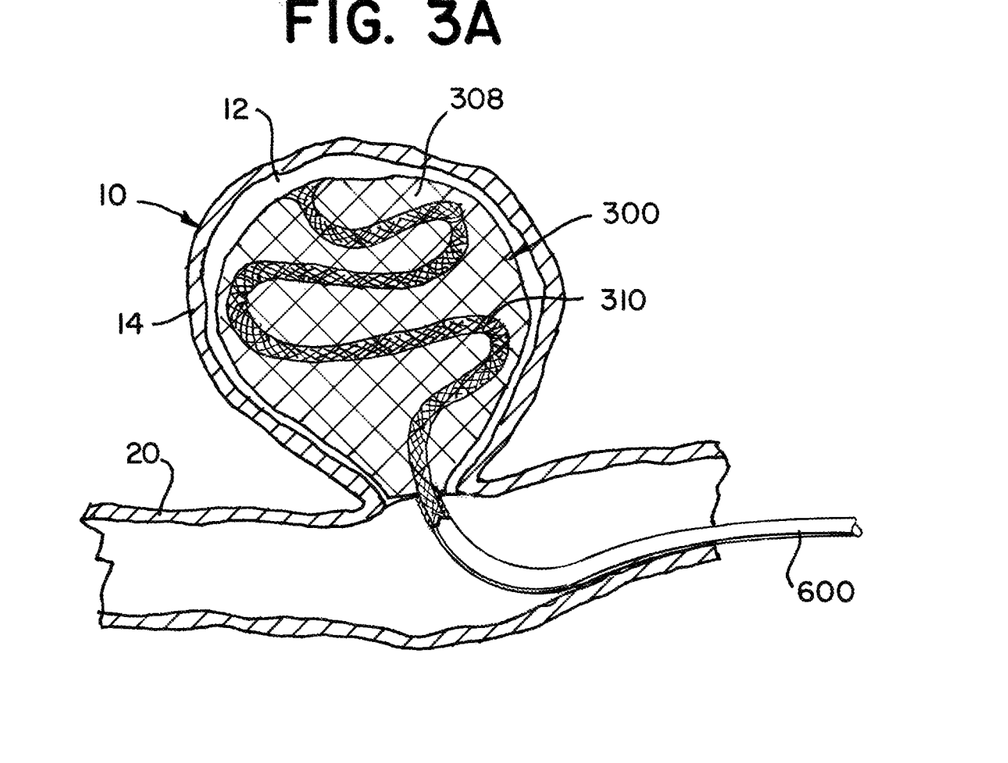
FIGS. 3a and 3b are a cut-away views illustrating a braided implant at various stages of implantation in an aneurysm according to the present invention.
Figure 3B:
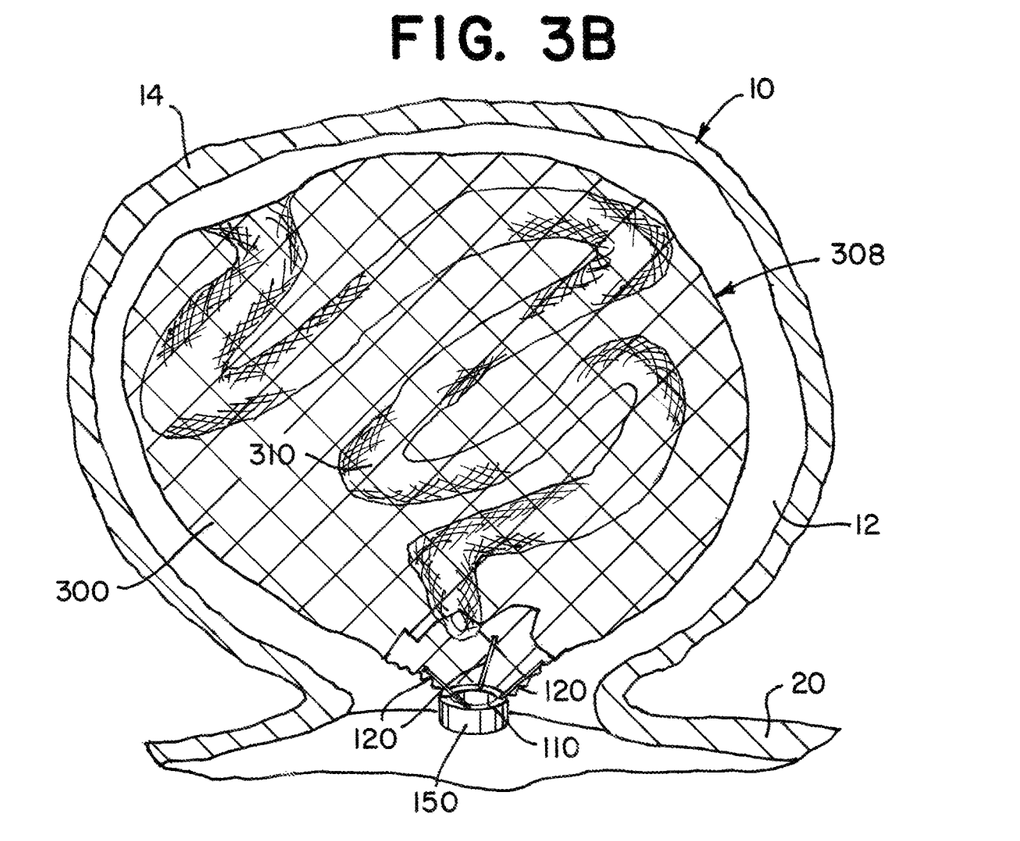

FIGS. 3a and 3b are a cut-away views illustrating a braided implant 300 at various stages of implantation in an aneurysm 10. FIG. 3a illustrates a braided implant 300 partially deployed into an aneurysm 10 of a blood vessel 20 but not yet released from its delivery system. The catheter 600 has been delivered to the site of the aneurysm 10. As shown, the braided implant 300 can form an occlusive sack 308 sized to extend to the walls 14 of the aneurysm 10. The portion of the braided implant 300 not forming an occlusive sack 308 can retain a tubular shape that can be packed into the aneurysm sac 12 forming an embolic filler braid 310. FIG. 3a illustrates the embolic filler braid 310 partially deployed such that a portion of the braid remains in the delivery system. In a partially deployed state, the braid 310 can be retracted back into the delivery tube 500, repositioned and redeployed. During retraction, repositioning, and redeployment, the releasing component 110 can remain attached or engaged with the delivery tube 500, thereby maintaining the attachment between the braided implant 300 and the delivery system.

FIG. 3b illustrates the implant 300 as deployed. The releasing component 110 can remain attached to the braided implant 300 and can reside at the neck of the aneurysm 10 once implanted. The releasing component 110 can have spring members 120 or other structures that extend outward, expanding the occlusive sack 308 at the neck of the aneurysm 10.

Figure 4A:
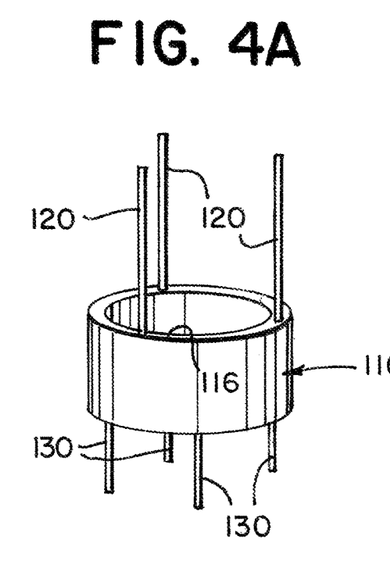
FIGS. 4a to 4c illustrate a releasing component according to the present invention.
Figure 4B:
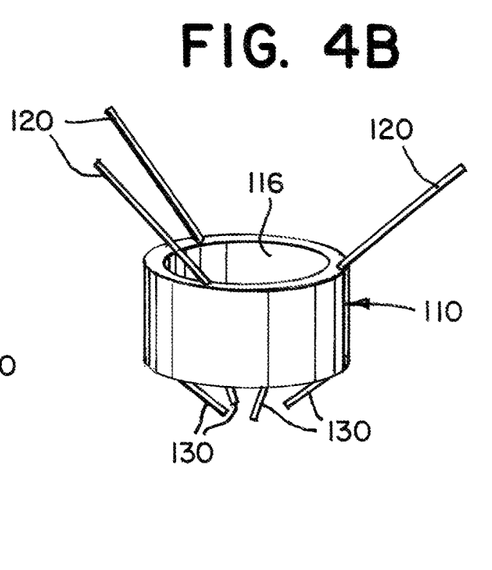
Figure 4C:
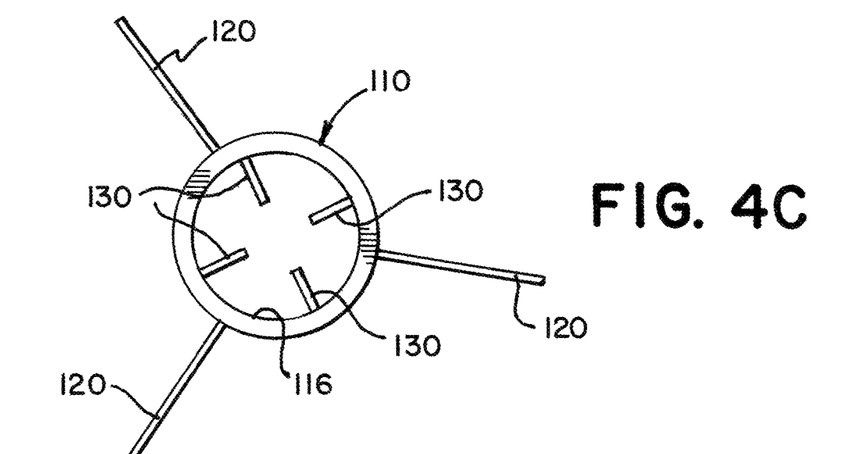

FIGS. 4a to 4c illustrate another example of a releasing component 110. As shown, the releasing component 110 can have occluding members 130. FIG. 4a illustrates the releasing component 110 in a configuration sized to fit over a delivery tube 500 and travel through a microcatheter 600. FIG. 4b is a side view of the releasing component 110 depicted in FIG. 4a in an example deployed configuration. FIG. 4c is a top view of the releasing component 110 in the deployed configuration. In the deployed configuration, the occluding members 130 can bend inwardly, at least partially occluding the lumen 116 of the releasing component 110. As discussed in relation to the spring members 120, the occluding members 130 can be composed of a flexible material and/or can be composed of a memory metal such as Nitinol. The occluding members 130 can be deformed in the delivery configuration and move to a pre-determined shape in the deployed configuration. The movement from the deformed to the pre-determined shape can be precipitated by a temperature change when the occluding members 130 contact blood or other bodily fluid.

The releasing component 110 can be oriented such that the occlusion of the lumen 116 of the releasing component 110 by the occluding members 130 would not result in the occluding members 130 inhibiting the releasing component 110 from disengaging and separating from the delivery tube 500. As shown, the occluding members 130 can be attached to the proximal side of the band 112 and the spring members 120 can be attached to the distal side. Oriented thusly, upon exiting the microcatheter 600, the spring members 120 can contact blood or bodily fluid, and as a result disengage the delivery tube 500. Meanwhile the catheter 600 can provide a barrier between the occluding members 130 and blood or fluid. The delivery tube 500 can then be extracted before the occluding members 130 contact blood or bodily fluid. Once the delivery tube 500 is extracted, the delivery catheter 600 can be extracted, thereby exposing the occluding members 130 to blood or fluid, causing the occluding members 130 to retract to occlude the lumen 116 of the band 112.

Figure 5A:
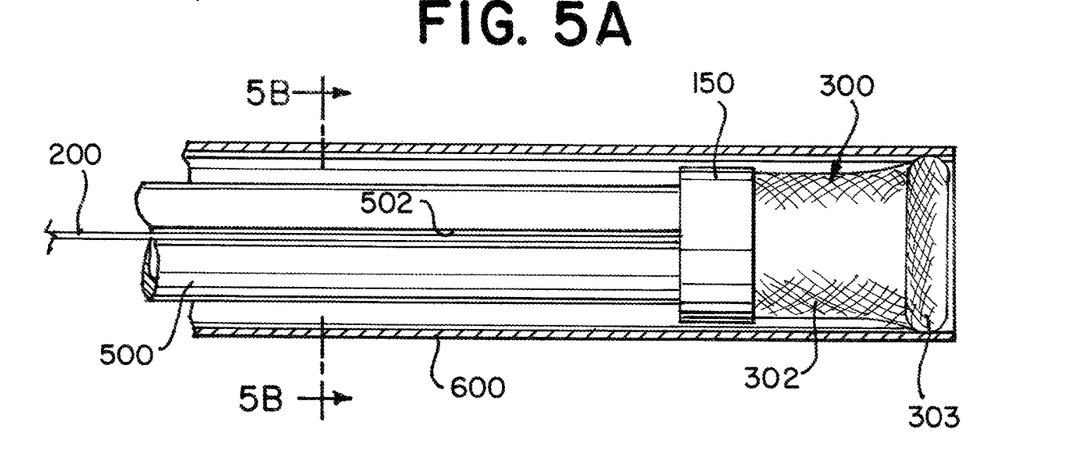
FIG. 5a is a cut-away view of an exemplary device of the present invention.

FIG. 5a shows the exterior of a device in front of a cut-away of the catheter 600. A pull wire 200 is positioned within a channel 502 on an outer surface 508 of a delivery tube 500. The pull wire 200 extends under the releasing component 110 to engage the releasing component 110. A braided implant 300 is attached to the releasing component 110 with an affixing component 150 and folded with an outer fold portion 302 positioned over the delivery tube 500 and a fold 303 positioned over a distal end of the delivery tube 500.

Figure 5B:
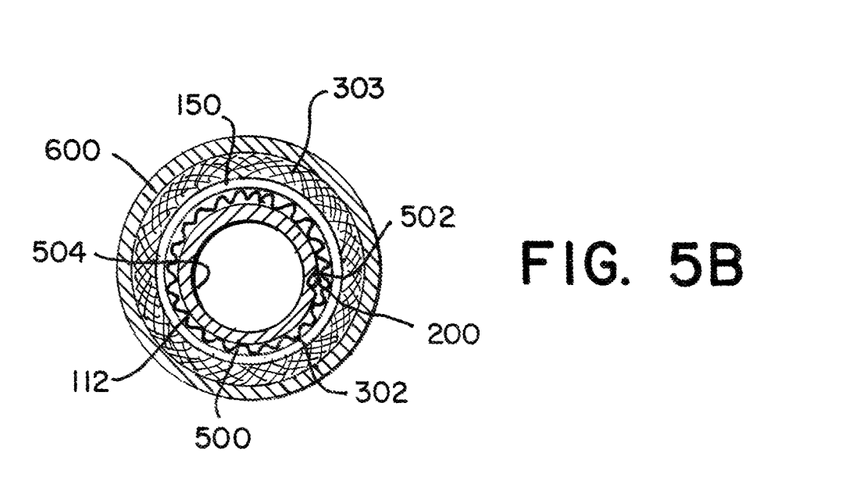
FIG. 5b is a cross-sectional view of an exemplary device of the present invention.

FIG. 5b shows a cross-sectional view of the system as indicated in FIG. 5a. FIG. 5b shows a potential positioning of the delivery tube 500, delivery tube channel 502, pull wire 200, band 112 of the releasing component 110, outer fold portion 302 of the braided implant 300, affixing component 150, and catheter 600.

Figure 6:
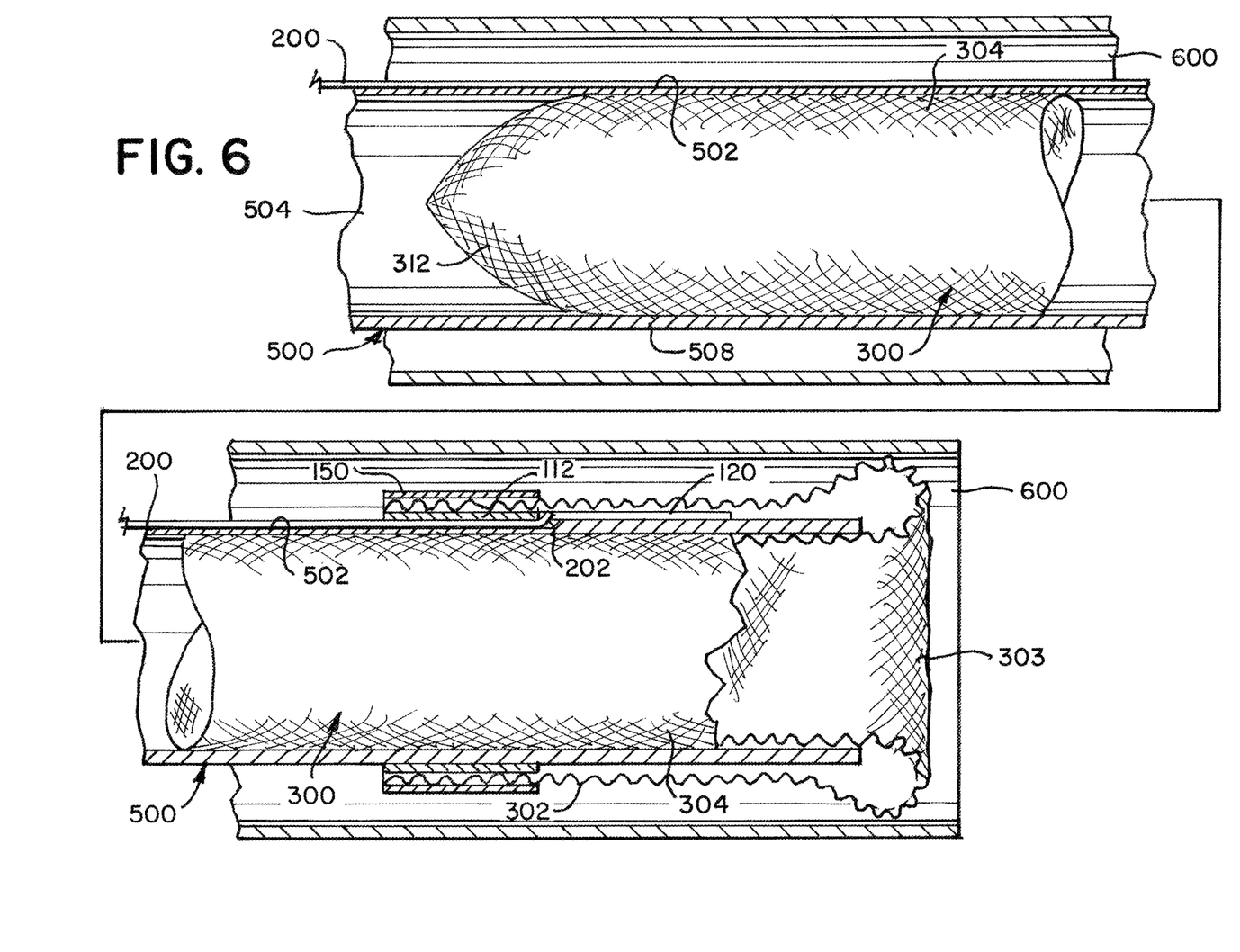
FIG. 6 is a cross-sectional view of an exemplary device of the present invention.

FIG. 6 is a cross-sectional view of the device and catheter 600 in the configuration shown in FIGS. 5a and 5b. In the cross-section views, the interior or lumen 504 of the delivery tube 500, the proximal end 312 of the braided implant 300, and cross-sections of the pull wire 200, delivery tube channel 502, releasing component 110, affixing component 150, braided implant inner fold 304, delivery tube 500, and braided implant outer fold 302 are visible. The extending portion 202 of the pull wire 200 is shown engaging the band 112 of the releasing component 110, and a spring member 120 is shown extending distally from the band 112 of the releasing component 110. The pull wire 200 can additionally extend to engage the braided implant 300.

Figure 7A:
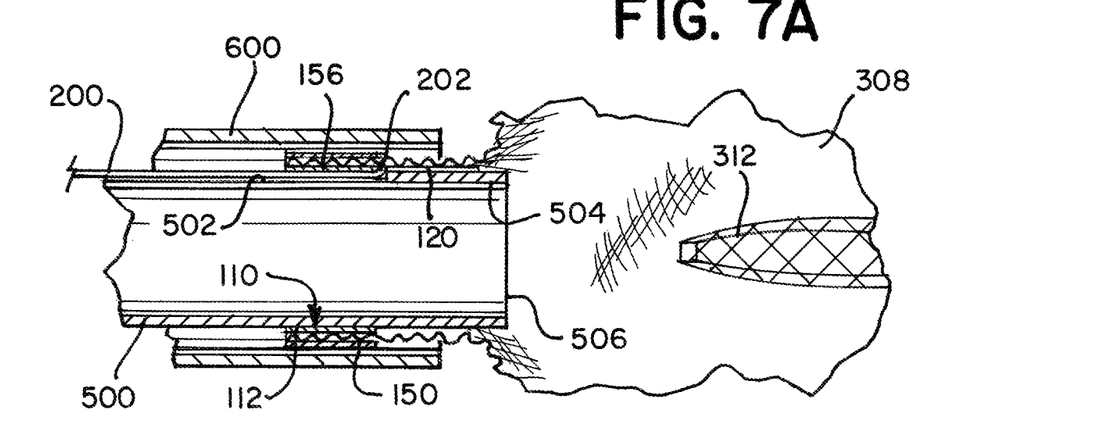
FIGS. 7a to 7c are cut-away views of an exemplary device at various stages of implantation according to the present invention.
Figure 7B:
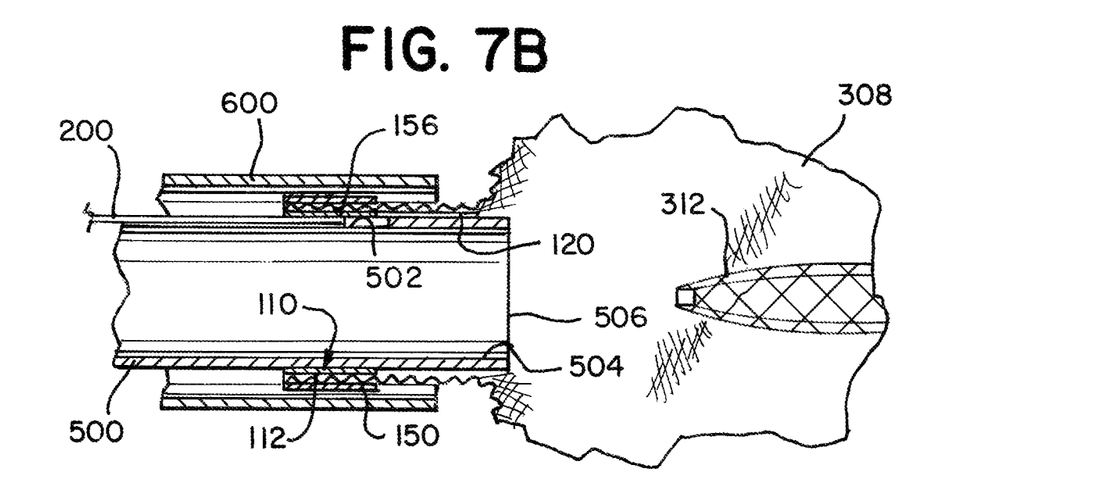
Figure 7C:
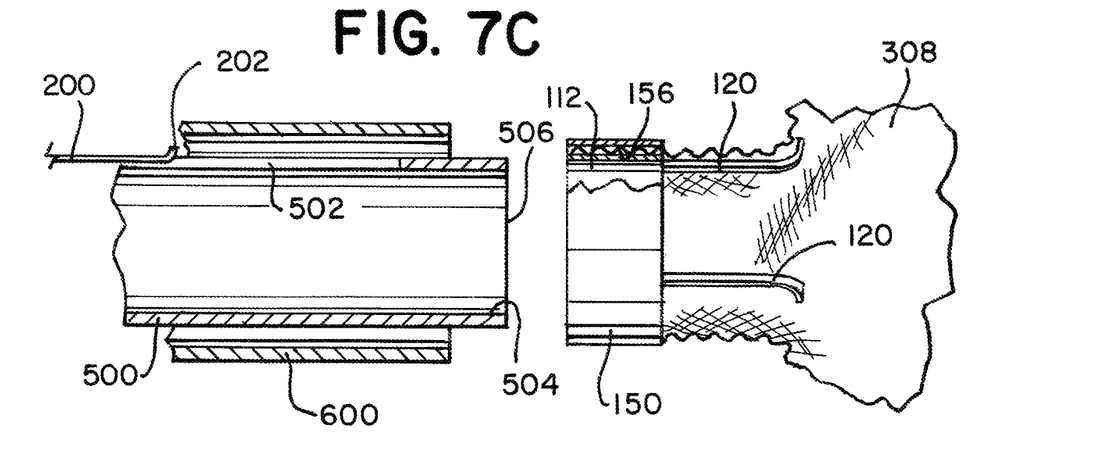

FIGS. 7a to 7c are cut-away views of an exemplary device at various stages following implantation of the braided implant 300, illustrating a releasing of the braided implant 300 from a delivery system. FIGS. 7a to 7c show cross sections of a delivery tube 500, delivery tube channel 502, pull wire 200, releasing component 110, affixing component 150, braided implant proximal end 312, and occlusive sack 308. At the stage illustrated in FIG. 7a, the braided implant 300 has been ejected from the delivery tube 500, and the braided implant 300 begins to detach from the delivery system. The distal end 506 of the delivery tube 500 extends distally out of a delivery catheter 600, and spring members 120 extend away from the delivery tube. The pull wire 200 can engage the releasing component 110 with an extending portion 202, inhibiting distal movement of the releasing component 110.

At the stage illustrated in FIG. 7b, the pull wire 200 has disengaged the releasing component 110. The extending portion 202 can be made of a flexible material that can straighten in response to a force, such that pulling the elongated portion 204 of the pull wire 200 proximally causes the extending portion 202 to retract from the distal surface 114 of the band 112 of the releasing component 110 and straighten to fit within the channel 502 of the delivery tube under the band 112 of the releasing component 110. Once the pull wire 200 is disengaged from the releasing component 110 as shown in FIG. 7b and the spring members 120 extend away from the delivery tube 500, the releasing component 110 can be free to slide off the distal end 506 of the delivery tube 500.

At the stage illustrated in FIG. 7c, the braided implant 300 has detached from the delivery tube 500. As shown, the spring members 120 can extend outwardly to juxtapose the braided implant 300. Once separated, the catheter 600, pull wire 200, and delivery tube 500 can be extracted from a patient.

Figure 8:
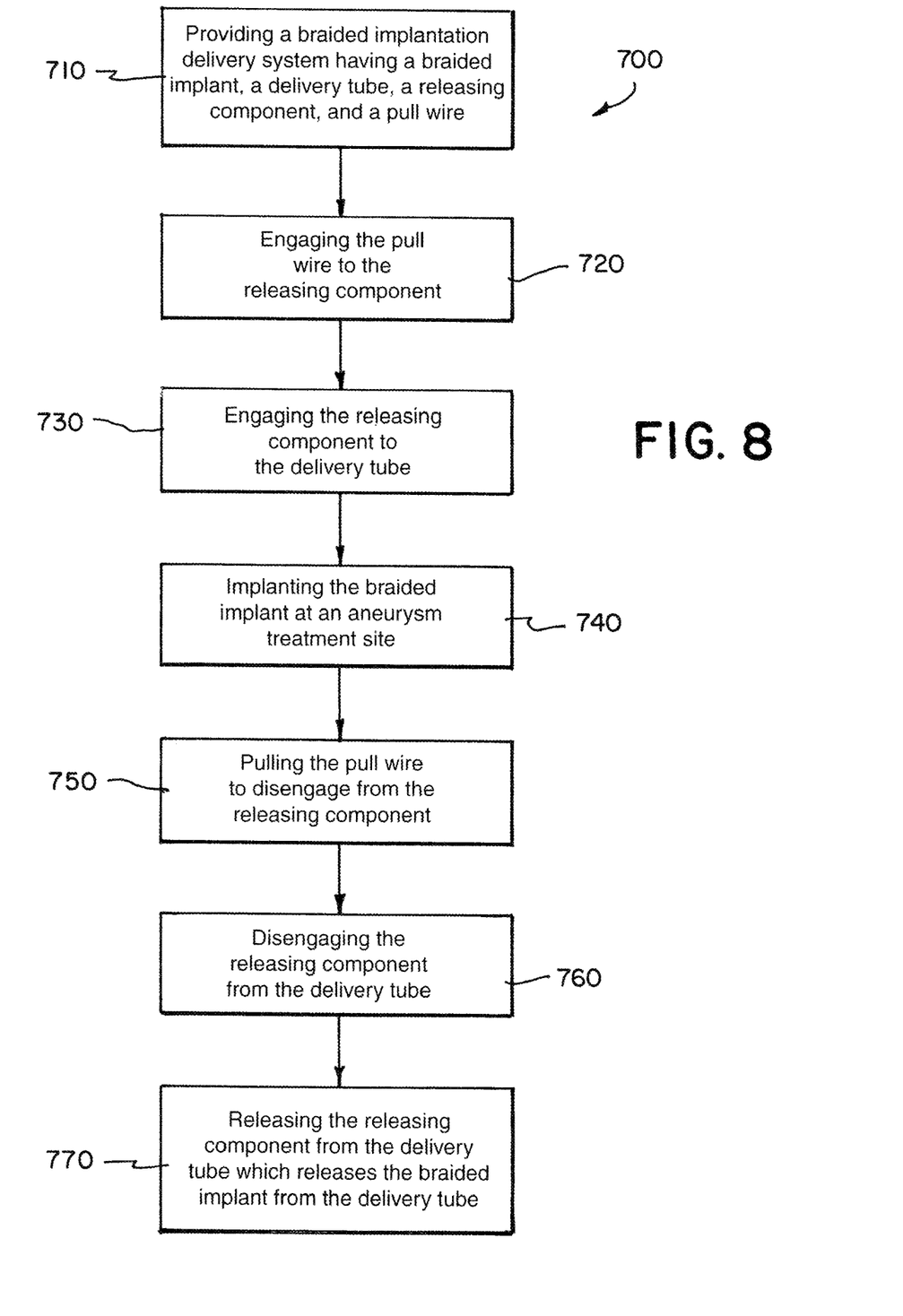
FIGS. 8 and 9 are flow diagrams outlining example method steps for use of a device according to the present invention.
Figure 9:
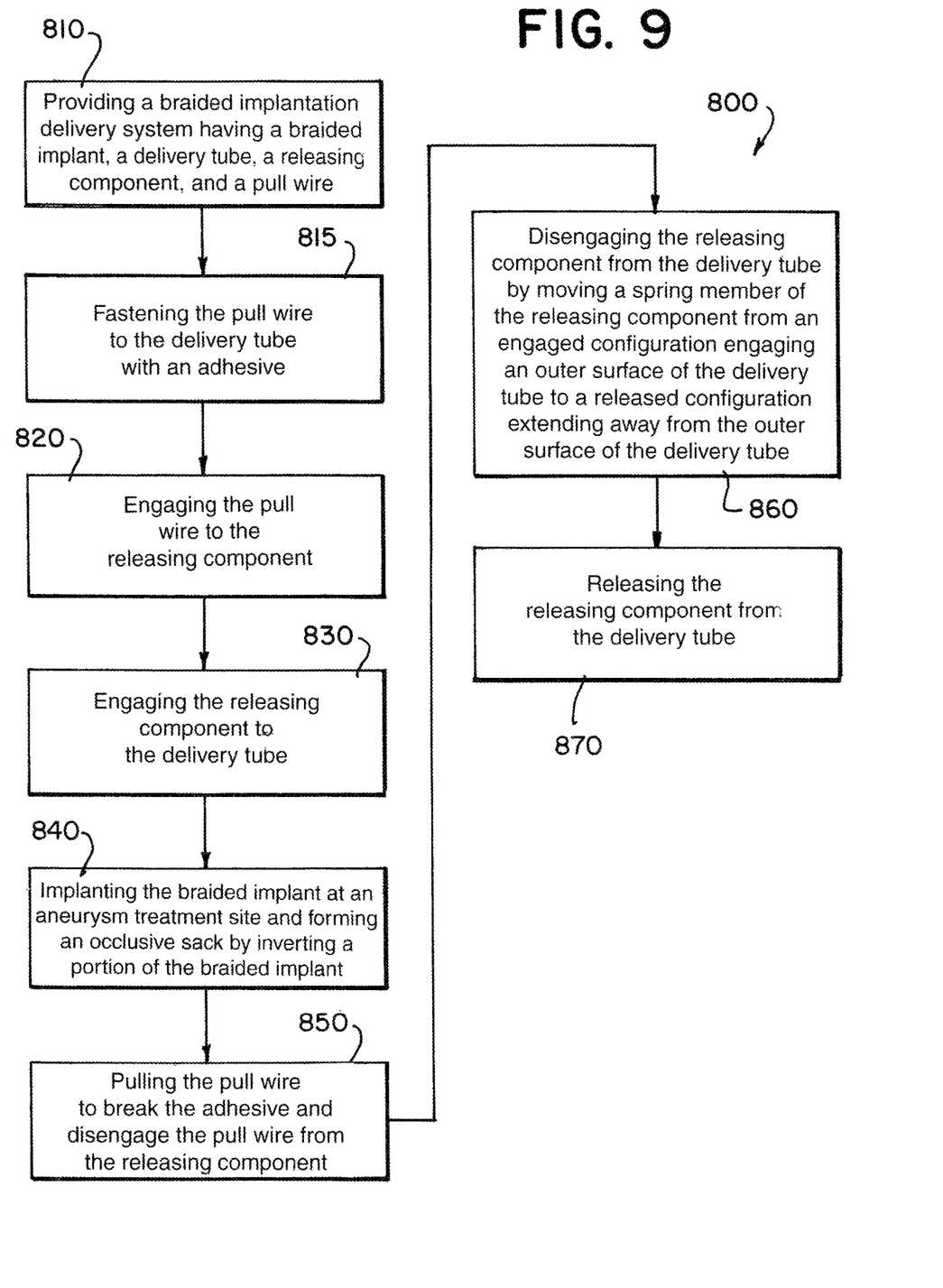

FIGS. 8 and 9 are flow diagrams outlining example method steps for use of a device according to the present invention. The method steps can be implemented by any of the example means described herein or by any means that would be known to one of ordinary skill in the art.

Referring to a method 700 outlined in FIG. 8, in step 710 a braided implantation delivery system having a braided implant, a delivery tube, a releasing component, and a pull wire 200 can be provided. The braided implant delivery system can be any of the delivery systems described herein having any combination of the features described herein, as well as any features that would be known to one skilled in the art. In step 720, the pull wire can be engaged to the releasing component. In step 730, the releasing component can be engaged to the delivery tube. In step 740, the braided implant can be implanted in an aneurysm at a treatment site. In step 750, the pull wire can be pulled to disengage the pull wire from the releasing component. In step 760, the releasing component can disengage from the delivery tube. In step 770, the releasing component can release from the delivery tube, thereby releasing the braided implant from the delivery tube.

Referring to a method 800 outlined in FIG. 9, in step 810 a braided implant delivery system having a braided implant, a delivery tube, a releasing component, and a pull wire can be provided. The braided implant delivery system can be any of the delivery systems described herein having any combination of the features described herein, as well as any features that would be known to one skilled in the art. In step 815, the pull wire can be fastened to the delivery tube with an adhesive. In step 820, the pull wire can engage the releasing component. In step 830, the releasing component can engage the delivery tube. In step 840 the braided implant can be implanted in an aneurysm at a treatment site, forming an occlusive sack by inverting a portion of the braided implant. In step 850, the adhesive can break, and the pull wire can disengage from the releasing component by pulling the pull wire. In step 860, the releasing component can disengage from the delivery tube by moving a spring member from an engaged configuration that engages an outer surface of the delivery tube to a released configuration that extends away from the outer surface of the delivery tube. In step 870, the releasing component can release from the delivery tube, thereby releasing the braided implant from the delivery tube.

The descriptions contained herein are examples illustrating the invention and are not intended to limit the scope of the invention. As described herein, the invention contemplates many variations and modifications of a system, device, or method that can be used to release a braided implant 300 in an aneurysm. Variations can include but are not limited to alternative geometries of elements and components described herein, utilizing any of numerous materials for each component or element (e.g. radiopaque materials, memory shape metals, etc.), utilizing additional components including components to position the braided implant 300 at a treatment site or eject a portion of the braided implant 300 from the interior of the delivery tube 500, utilizing additional components to perform functions described herein, or utilizing additional components to perform functions not described herein, for example. These modifications would be apparent to those having ordinary skill in the art to which this invention relates and are intended to be within the scope of the claims which follow.

The invention claimed is:

1. A system for releasing a braided implant in an aneurysm, the system comprising:
    the braided implant;
    a delivery tube comprising a lumen therethrough, a distal end, an outer surface, and a channel disposed on the outer surface;
    a releasing component comprising:
        a band comprising an outer surface attached to a first portion of the braided implant and a lumen encompassing the delivery tube approximate the distal end of the delivery tube, and
        a spring member attached to the band, the spring member movable from a compression configuration to an extended configuration, the compression configuration pressing the outer surface of the delivery tube, and the extended configuration extending away from the outer surface of the delivery tube; and
    a pull wire positioned within the channel of the delivery tube, the pull wire movable from an engaging configuration to a releasing configuration, the engaging configuration engaging the releasing component, and the releasing configuration allowing the spring member to expand to its extended configuration.

2. The system of claim 1,
    wherein the first portion of the braided implant is separated from a second portion of the braided implant by a fold,
    wherein the first portion encompasses a portion of the outer surface of the distal end of the delivery tube, and
    wherein the second portion comprises an elongated tubular structure and is positioned within the lumen of the delivery tube.

3. The system of claim 1 wherein the pull wire comprises an extending portion and an elongated portion, wherein a movement of the elongated portion moves the extending portion from the engaging configuration to the releasing configuration.

4. The system of claim 3 wherein the pull wire is fastened to the channel of the delivery tube with an adhesive, and wherein the movement of the elongated portion breaks the adhesive to unfasten the pull wire.

5. The system of claim 1 further comprising an affixing component affixing the braided implant to the outer surface of the band, the affixing component comprising a lumen therethrough, the lumen of the affixing component encompassing the band.

6. The system of claim 1 wherein the spring member is an elongated member, the elongated member comprises a proximal end and a distal end, the proximal end of the elongated member is attached to a distal surface of the band, the distal end of the elongated member presses against the outer surface of the delivery tube in the compression configuration, and the distal end of the elongated member extends away from the outer surface of the delivery tube in the extended configuration.

7. They system of claim 1 wherein the releasing component further comprises an occlusion member attached to the band movable from a delivery configuration to a deployed configuration, the delivery configuration extending longitudinally along the outer surface of the delivery tube, and the deployed configuration at least partially obstructing the lumen of the band.

8. The system of claim 1 wherein the releasing component comprises a radiopaque material.

9. A device for treating an aneurysm, the device comprising:
- a tubular delivery member comprising a distal delivery end, an interior, and an exterior;
- a braided tubular implant comprising:
  - a distal implant end extending outward from the distal delivery end of the tubular delivery member and folding proximally over a portion of the exterior of the tubular delivery member, and
  - a proximal implant end positioned within the interior of the tubular delivery member;
- a band attached to the distal implant end and detachably attached to the exterior of the tubular delivery member approximate the distal delivery end so that the tubular delivery member extends through a lumen of the band; and
- a wire segment positioned approximate the distal delivery end of the tubular delivery member, the wire segment comprising a bent configuration and a straight configuration, the bent configuration engaging a distal surface of the band, and the straight configuration being disengaged from the distal surface of the band.

10. The device of claim 9 wherein the band comprises an attached configuration and a deployed configuration, the attached configuration engaging the exterior of the tubular delivery member and the deployed configuration disengaging the exterior of the tubular delivery member.

11. The device of claim 10 wherein the deployed configuration at least partially occludes the lumen of the band.

12. The device of claim 9, further comprising a pull wire comprising the wire segment and an elongated portion extending proximally from the wire segment,
   wherein a movement of the elongated portion of the pull wire moves the wire segment from the bent configuration to the straight configuration.

13. The device of claim 12 wherein the pull wire is positioned within a channel on the exterior of the tubular delivery member.

14. The device of claim 12 wherein the pull wire is fastened to the tubular delivery member with an adhesive, and wherein the movement of the elongated portion breaks the adhesive to unfasten the pull wire.

* * * * *